(12) United States Patent
Taylor et al.

(10) Patent No.: US 8,545,488 B2
(45) Date of Patent: Oct. 1, 2013

(54) CARDIOVASCULAR IMAGING SYSTEM

(75) Inventors: Kevin D. Taylor, Colorado Springs, CO (US); Ken Harlan, Peyton, CO (US); James Nye, Colorado Springs, CO (US); Robert Splinter, Concord, NC (US); Jacob Keeler, Colorado Springs, CO (US); Chris J. Hebert, Lafayette, LA (US); Wade A. Bowe, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 612 days.

(21) Appl. No.: 12/649,759

(22) Filed: Dec. 30, 2009

(65) Prior Publication Data

US 2011/0009750 A1    Jan. 13, 2011

Related U.S. Application Data

(63) Continuation-in-part of application No. 12/337,232, filed on Dec. 17, 2008, which is a continuation-in-part of application No. 11/228,845, filed on Sep. 16, 2005, now Pat. No. 7,572,254.

(60) Provisional application No. 60/611,191, filed on Sep. 17, 2004.

(51) Int. Cl.
 *A61B 18/18* (2006.01)
(52) U.S. Cl.
 USPC .......... 606/7; 606/2; 606/13; 606/14; 606/15; 607/89
(58) Field of Classification Search
 None
 See application file for complete search history.

(56) References Cited

U.S. PATENT DOCUMENTS

| | | | |
|---|---|---|---|
| 4,053,845 A | 10/1977 | Gould |
| 4,641,912 A | 2/1987 | Goldenberg |
| 4,669,465 A | 6/1987 | Moore et al. |
| 4,686,979 A | 8/1987 | Gruen et al. |
| 4,732,448 A | 3/1988 | Goldenberg |
| 4,747,405 A | 5/1988 | Leckrone |
| 4,769,005 A | 9/1988 | Ginsburg et al. |
| 4,784,132 A | 11/1988 | Fox et al. |
| 4,788,975 A | 12/1988 | Shturman et al. |
| 4,799,754 A | 1/1989 | Goldenberg |

(Continued)

FOREIGN PATENT DOCUMENTS

| GB | 2208807 A | 4/1989 |
|---|---|---|
| WO | WO 98/19614 A | 5/1998 |

OTHER PUBLICATIONS

International Search Report for International (PCT) Patent Application No. PCT/US05/33029, mailed Oct. 3, 2006, 1 page.

(Continued)

*Primary Examiner* — Bill Thomson
*Assistant Examiner* — Lynsey Crandall
(74) *Attorney, Agent, or Firm* — Sheridan Ross P.C.

(57) ABSTRACT

Embodiments of the present invention include a laser catheter that includes a catheter body, a light guide, and a distal tip that extends beyond the exit aperture of the light guide. In some embodiments, an imaging device is disposed on the distal tip such that the imaging device is distal relative to the exit aperture of the light guide. In some embodiments, the imaging device can be gated to record images during and/or slightly beyond periods when the laser catheter is not activated.

14 Claims, 13 Drawing Sheets

(56) References Cited

U.S. PATENT DOCUMENTS

| | | |
|---|---|---|
| 4,807,620 A | 2/1989 | Strul |
| 4,830,460 A | 5/1989 | Goldenberg |
| 4,844,062 A | 7/1989 | Wells |
| 4,848,336 A | 7/1989 | Fox et al. |
| 4,924,863 A | 5/1990 | Sterzer |
| 5,016,964 A | 5/1991 | Donnelly |
| 5,024,234 A | 6/1991 | Leary et al. |
| 5,026,366 A | 6/1991 | Leckrone |
| 5,040,548 A | 8/1991 | Yock |
| 5,041,108 A | 8/1991 | Fox et al. |
| 5,188,632 A | 2/1993 | Goldenberg |
| 5,207,672 A | 5/1993 | Roth et al. |
| 5,217,454 A | 6/1993 | Khoury |
| 5,250,045 A | 10/1993 | Bohley |
| 5,263,952 A | 11/1993 | Grace |
| 5,267,341 A | 11/1993 | Shearin |
| 5,300,085 A | 4/1994 | Yock |
| 5,304,171 A | 4/1994 | Gregory et al. |
| 5,318,032 A | 6/1994 | Lonsbury et al. |
| 5,350,375 A | 9/1994 | Deckelbaum et al. |
| 5,350,377 A | 9/1994 | Winston et al. |
| 5,350,395 A | 9/1994 | Yock |
| 5,352,197 A | 10/1994 | Hammersmark et al. |
| 5,377,683 A | 1/1995 | Barken |
| 5,415,653 A | 5/1995 | Wardle et al. |
| 5,425,355 A | 6/1995 | Kulick |
| 5,429,604 A | 7/1995 | Solar |
| 5,429,617 A | 7/1995 | Hammersmark et al. |
| 5,440,664 A | 8/1995 | Harrington et al. |
| 5,451,233 A | 9/1995 | Yock |
| 5,456,680 A | 10/1995 | Taylor et al. |
| 5,464,395 A | 11/1995 | Faxon et al. |
| 5,470,330 A | 11/1995 | Goldenberg et al. |
| 5,484,433 A | 1/1996 | Taylor et al. |
| 5,514,128 A | 5/1996 | Hillsman et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory |
| 5,657,760 A | 8/1997 | Ying et al. |
| 5,722,972 A | 3/1998 | Power et al. |
| 5,755,714 A | 5/1998 | Murphy-Chutorian |
| 5,792,118 A | 8/1998 | Kurth et al. |
| 5,803,083 A | 9/1998 | Buck et al. |
| 5,817,144 A | 10/1998 | Gregory |
| 5,824,026 A | 10/1998 | Diaz |
| 5,836,946 A | 11/1998 | Diaz et al. |
| RE36,104 E | 2/1999 | Solar |
| 5,891,133 A | 4/1999 | Murphy-Chutorian |
| 5,938,609 A | 8/1999 | Pomeranz |
| 5,976,124 A | 11/1999 | Reiser |
| 5,989,243 A | 11/1999 | Goldenberg |
| 6,022,342 A | 2/2000 | Mukherjee |
| 6,033,402 A | 3/2000 | Tu et al. |
| 6,036,715 A | 3/2000 | Yock |
| 6,056,743 A | 5/2000 | Ellis et al. |
| 6,066,130 A | 5/2000 | Gregory et al. |
| 6,117,128 A | 9/2000 | Gregory |
| 6,231,563 B1 | 5/2001 | White et al. |
| 6,287,297 B1 | 9/2001 | Woodruff et al. |
| 6,290,668 B1 | 9/2001 | Gregory et al. |
| 6,302,875 B1 | 10/2001 | Makower et al. |
| 6,419,684 B1 | 7/2002 | Heisler et al. |
| 6,432,115 B1 | 8/2002 | Mollenauer et al. |
| 6,447,504 B1 | 9/2002 | Ben-Haim et al. |
| 6,447,525 B2 | 9/2002 | Follmer et al. |
| 6,458,098 B1 | 10/2002 | Kanesaka |
| 6,575,993 B1 | 6/2003 | Yock |
| 6,743,208 B1 | 6/2004 | Coyle |
| 7,238,178 B2 | 7/2007 | Maschke |
| 8,016,748 B2 * | 9/2011 | Mourlas et al. ............... 600/115 |
| 2001/0014805 A1 | 8/2001 | Burbank et al. |
| 2002/0045811 A1 | 4/2002 | Kittrell et al. |
| 2002/0103459 A1 | 8/2002 | Sparks et al. |
| 2003/0032936 A1 | 2/2003 | Lederman |
| 2003/0078566 A1 | 4/2003 | Elliott et al. |
| 2003/0219202 A1 * | 11/2003 | Loeb et al. ...................... 385/33 |
| 2004/0059280 A1 | 3/2004 | Makower et al. |
| 2004/0133154 A1 | 7/2004 | Flaherty et al. |
| 2004/0162548 A1 | 8/2004 | Reiser |
| 2005/0149176 A1 | 7/2005 | Heggestuen et al. |
| 2006/0094930 A1 | 5/2006 | Sparks et al. |
| 2006/0167442 A1 | 7/2006 | Hebert et al. |
| 2008/0108867 A1 | 5/2008 | Zhou |
| 2009/0163900 A1 | 6/2009 | Taylor et al. |
| 2009/0198221 A1 | 8/2009 | Hebert et al. |
| 2010/0114081 A1 | 5/2010 | Keeler et al. |
| 2010/0152717 A1 | 6/2010 | Keeler |

OTHER PUBLICATIONS

Extended European Search Report for European Patent Application No. 05796879.4, dated Mar. 6, 2008, 7 pages.
Extended European Search Report for European Patent Application No. 08010688.3, dated Feb. 17, 2009, 6 pages.
International Preliminary Report on Patentability for International (PCT) Patent Application No. PCT/US2009/066133, mailed Jun. 30, 2011, 8 pages.
Grundfest, Warren S., MD, et al., "Laser Ablation of Human Atherosclerotic Plaque Without Adjacent Tissue Injury," JACC vol. 5, No. 4, pp. 929-933, Apr. 1985.
PCT International Search Report and Written Opinion mailed Jan. 26, 2010; International Application No. PCT/US2009/066133; 9 pages.
Official Action for U.S. Appl. No. 11/228,845, mailed Sep. 3, 2008.
Official Action for U.S. Appl. No. 11/228,845, mailed Jan. 12, 2009.
Notice of Allowance for U.S. Appl. No. 11/228,845, mailed Jun. 5, 2009.
Notice of Allowance for U.S. Appl. No. 12/406,807, mailed Aug. 2, 2010.
Official Action for U.S. Appl. No. 12/337,232, mailed Mar. 23, 2012.
Official Action for U.S. Appl. No. 12/337,232, mailed Sep. 13, 2012 10 pages.

* cited by examiner

*A-A*

*B-B*

*C-C*

*D-D*

*E-E*

*F-F*

A-A

B-B

C-C

D-D

E-E

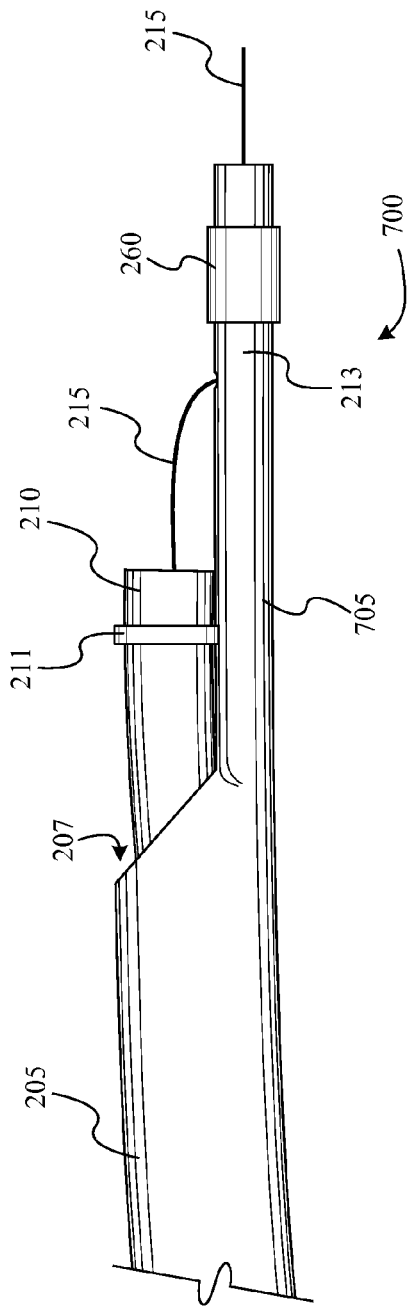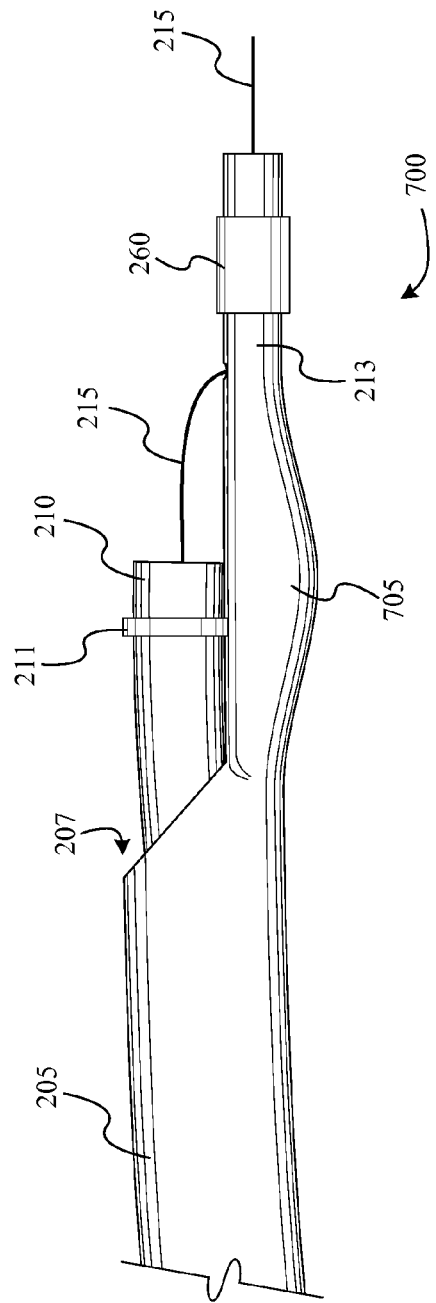

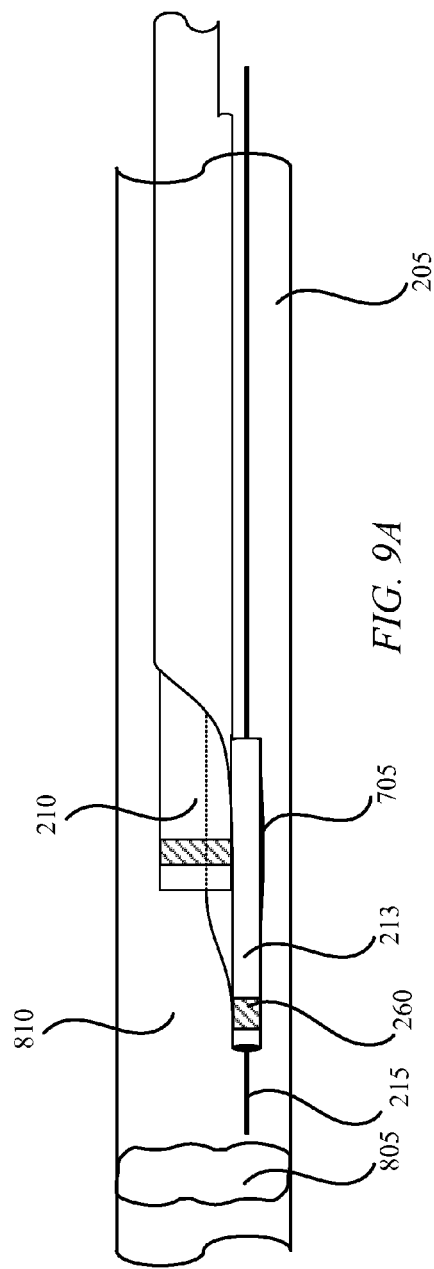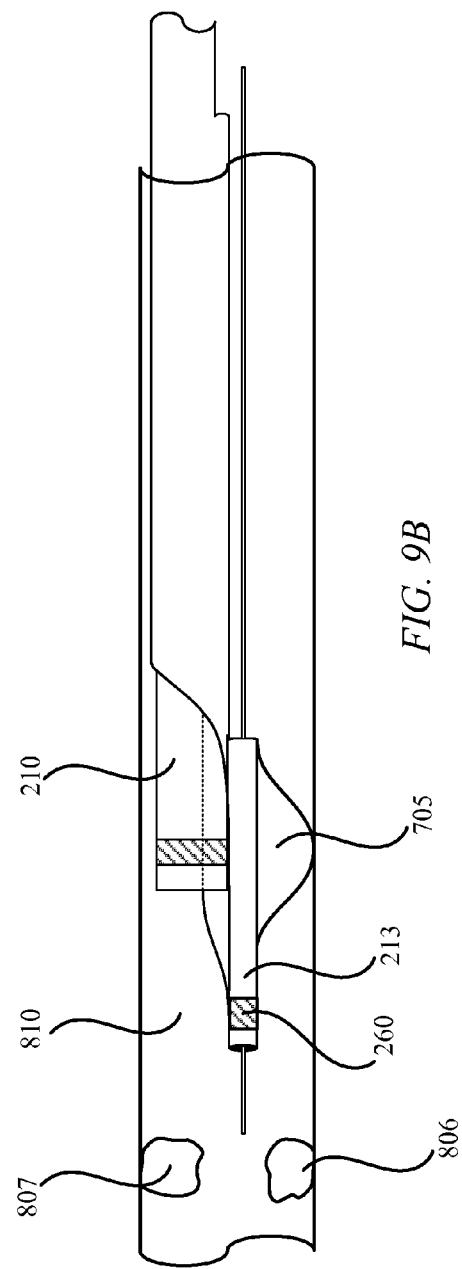

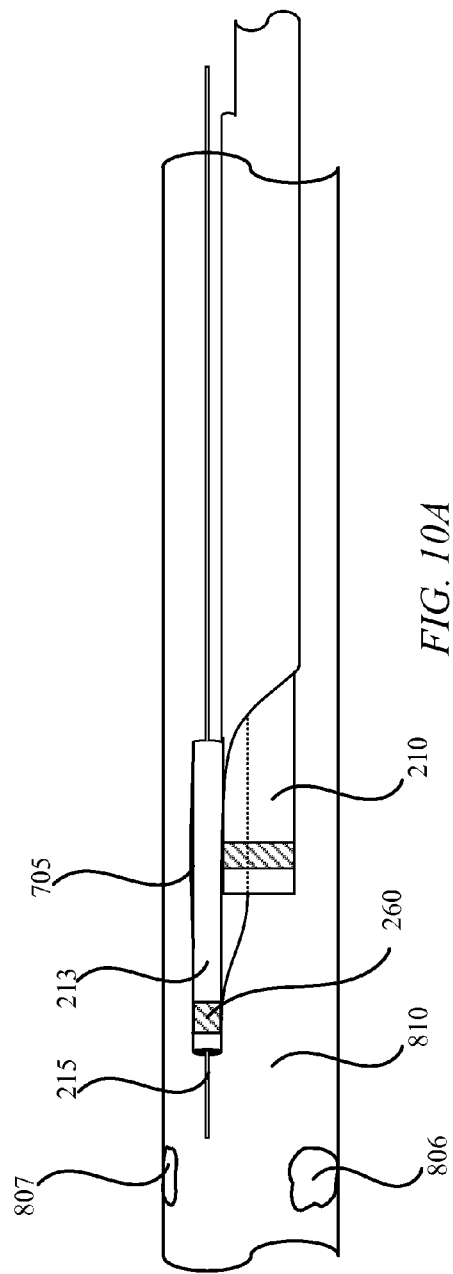
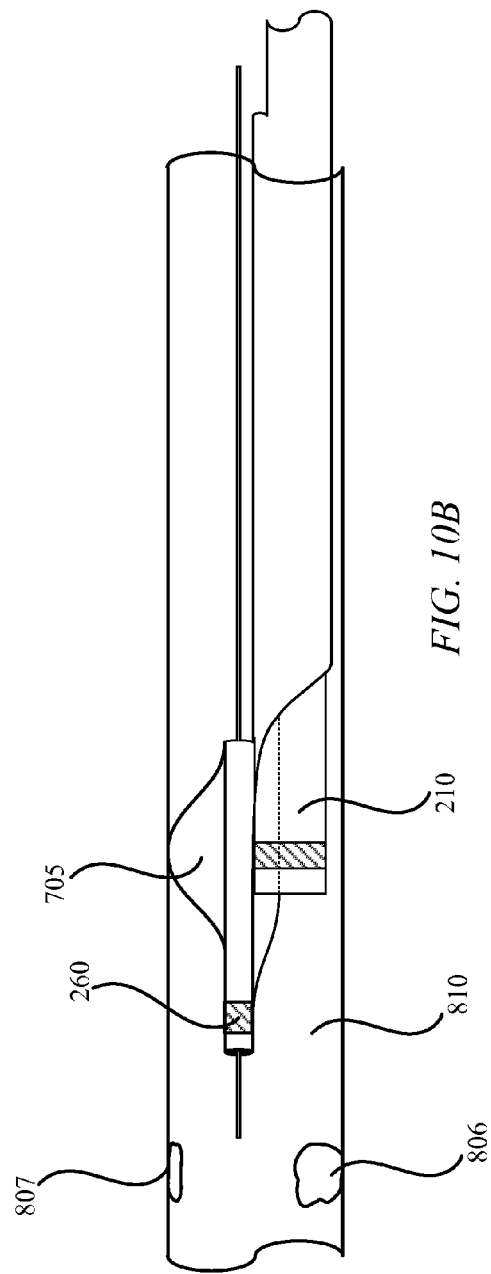
FIG. 10A
FIG. 10B

CARDIOVASCULAR IMAGING SYSTEM

CROSS-REFERENCES TO RELATED APPLICATIONS

This application is a continuation in part of U.S. Non-Provisional application Ser. No. 12/337,232 filed on Dec. 17, 2008, which is a continuation in part of U.S. Non-Provisional application Ser. No. 11/228,845 filed on Sep. 16, 2006, which claims the benefit of U.S. Provisional Application Ser. No. 60/611,191 filed Sep. 17, 2004. Each of these disclosures are incorporated by reference in their entirety.

BACKGROUND

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is ineffective or too risky (often introduction of a balloon in an occluded artery can cause portions of the atherosclerotic material to become dislodged, which may cause a total blockage at a point downstream of the subject occlusion, thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

Due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up balloon angioplasty is recommended.

Imaging during atherectomy or angioplasty procedures often uses fluoroscopy imaging techniques for targeting and ablation of blockages. Fluoroscopy, however, has limitations. For example, does not allow a doctor or technician to visualize plaque or vessel walls.

BRIEF SUMMARY

Embodiments of the invention are directed toward laser catheters. In one embodiment, a laser catheter can include a catheter body, a light guide, a distal tip, and an imaging device disposed distal relative to the exit aperture of the light guide. The catheter body, for example may include a central axis, a proximal end and a distal end. The catheter body may also include a lumen disposed between the proximal end and the distal end, the lumen having an opening at the distal end. The light guide may also include a proximal end and a distal end. In some embodiments, the light guide may also include at least one fiber optic and may at least partially be disposed within the lumen and/or movable therein. The distal tip may be positioned at the periphery of the catheter body and may extend from the distal end of the catheter body. The imaging device can be disposed on the distal tip, for example, at a position distal from the exit aperture of the light guide. The distal tip may also include a guidewire lumen that includes a guidewire port at the distal end of the distal tip. A retaining wire may also be used in some embodiments and can be coupled with the distal tip and slidably coupled with the light guide. A balloon, for example, may be positioned between the opening at the first distal end of the catheter body and the distal tip.

Some embodiments of the invention can also include a balloon catheter. The balloon catheter can include a catheter body, for example may include a central axis, a proximal end and a distal end. The catheter body may also include a lumen disposed between the proximal end and the distal end, the lumen having an opening at the distal end. The balloon catheter can also include a light guide that may also include a proximal end and a distal end. In some embodiments, the light guide may also include at least one fiber optic and may at least partially be disposed within the lumen and/or movable therein. The balloon can be disposed at the radial exterior of the catheter body. In use, for example, the balloon can be inflated such that the balloon makes contact with a vessel wall. Contact with the vessel wall can move the distal tip of the catheter away from vessel wall toward an opposing vessel wall.

Some embodiments of the invention can also include an imaging catheter that gates imaging during ablation. For example, an imaging catheter can include a light guide coupled with a laser and an imaging device disposed distally relative to the light guide exit aperture. During operation, in some embodiments, images from the light guide can be filtered and/or gated while the laser is activated. In other embodiments, the imaging device can be deactivated during ablation.

The following detailed description, together with the accompanying drawings, will provide a better understanding of the nature and advantage of the embodiments disclosed herein.

BRIEF DESCRIPTION OF THE DRAWINGS

FIG. 7A shows a side view of a balloon catheter with the balloon deflated according to another embodiment of the invention.

FIG. 7B shows a side view of a balloon catheter with the balloon inflated according to another embodiment of the invention.

FIGS. 9A, 9B, 10A, and 10B show a cutaway view of a balloon biasing catheter in use within a vessel according to one embodiment.

DETAILED DESCRIPTION

Embodiments of the present invention include a laser catheter that employs an imaging device. In some embodiments, the imaging device is disposed distal (or forward) relative to the exit aperture of the laser catheter. In some embodiments, the laser catheters can employ gating techniques to ensure that laser pulses don't interfere with imaging. Other embodiments include laser catheters that include balloons or ramps that can deflect the exit aperture of the laser catheter.

Figure 1:
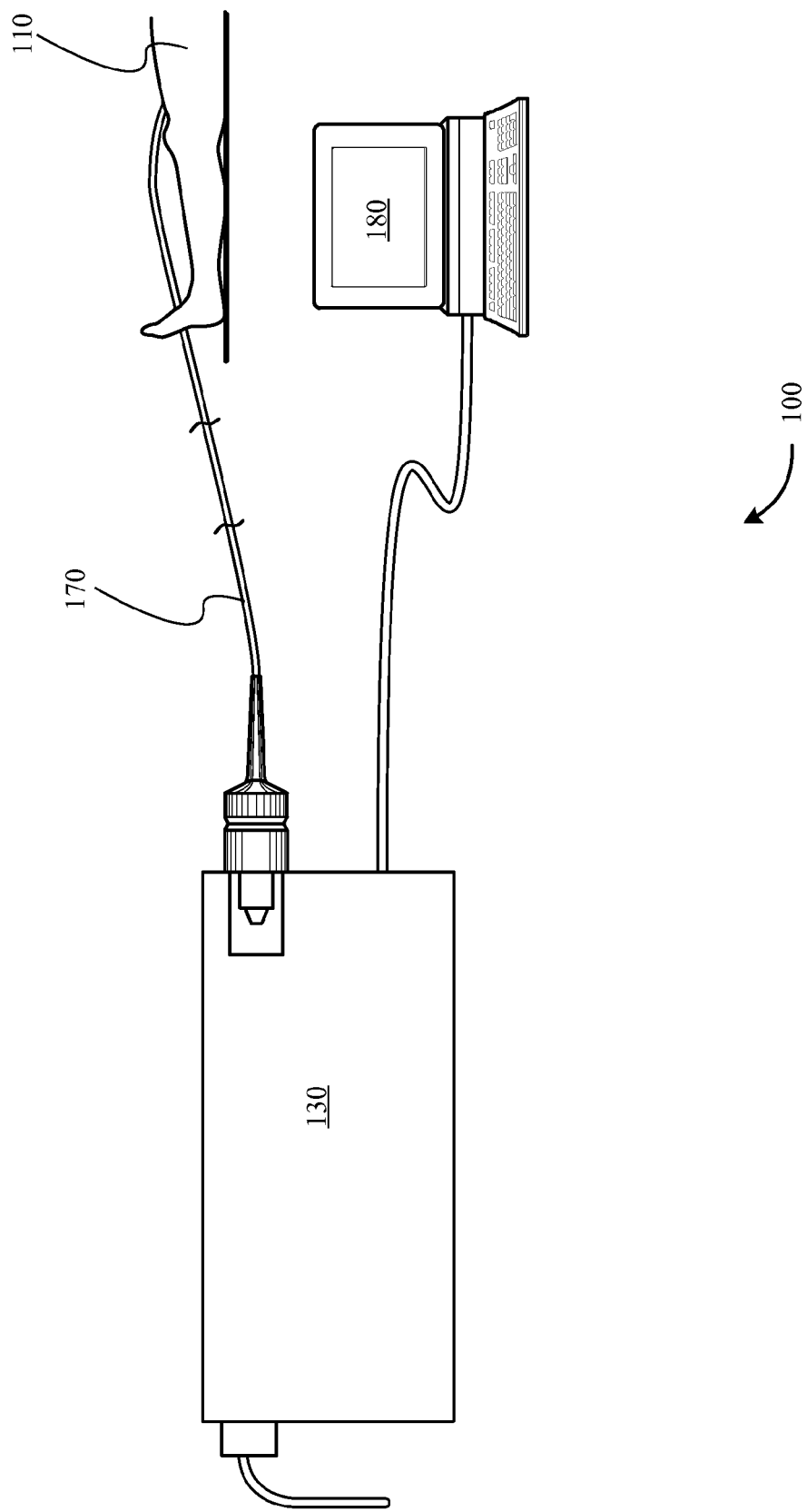
FIG. 1 shows a laser catheter system according to one embodiment.

FIG. 1 shows a laser catheter system 100 in use according to one embodiment. A laser 130 is shown coupled with a user interface 180. In this embodiment the user interface 180 is computer programmed to control the laser 130. The laser, for example, may be an excimer laser. The laser, for example, may also produce light in the ultraviolet range. The laser is connected with a catheter 170 that may be inserted into a vessel of the human body 110. The laser catheter system 100 may employ one or more tapered waveguides that guide laser light from the laser 130 through the catheter 170 toward a target.

Figure 2A:
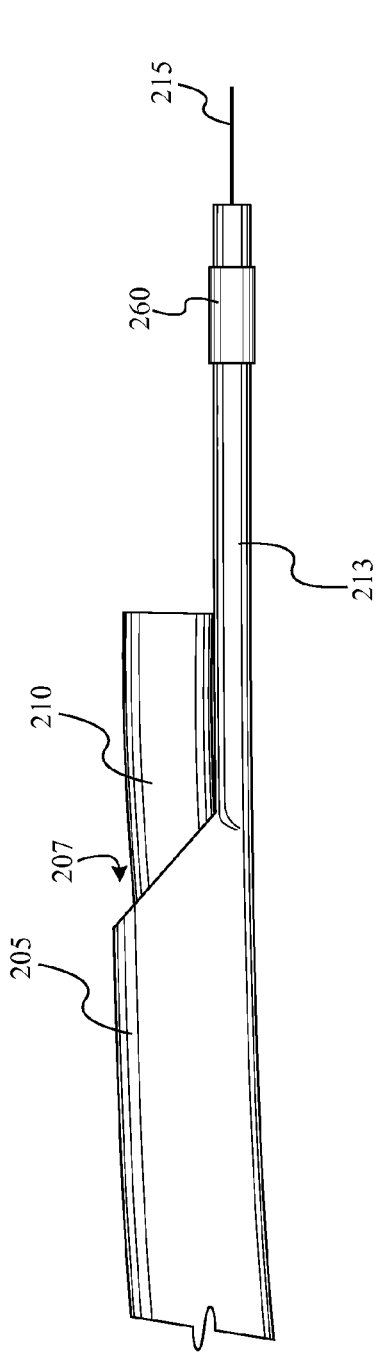
FIGS. 2A and 2B show examples of laser catheters with a distal imaging device according to some embodiments of the invention.

FIG. 2A shows laser catheter 200 with distal imaging device 260 according to some embodiments. Laser catheter 200 can include a catheter body 205 (or sheath) within which a fiber optic bundle 210 (or any other light guide) is disposed. Fiber optic bundle can include any number of optical fibers and, in some embodiments, can include a separate sheath. Catheter body 205 can include a distal end and a proximal end. The proximal end of catheter body 205 can include a coupler that is configured to couple with a laser source as shown in FIG. 1. The proximal end of the fiber optic bundle can also be coupled with the coupler in order to receive and conduct laser light through the optical fibers. The distal end of catheter body 205 includes opening 207 from which the distal end of fiber optic bundle 210 extends.

As shown in FIG. 2A, imaging device 260 is disposed distal relative to the exit aperture of optical light guide 210 (e.g., a fiber optic bundle). Light guide 210 can be disposed within sheath 205. In some embodiments, imaging device 260 can be disposed on eccentric distal tip 213. In other embodiments, imaging device 260 can be disposed on an axially placed distal tip. Distal tip can also extend In yet other embodiments, imaging device 260 can be disposed distal relative to the exit aperture of light guide 210 in any configuration. In some embodiments, imaging device 260 can be positioned at least 0.4, 0.5, 0.6, 0.7, 0.8, 0.9, 1.0 cm longitudinally (or forward) from the distal end (or exit aperture) of light guide 210.

Imaging device 260, for example, can be an ultrasonic device such as an Intracoronary/Intravascular Ultrasound (ICUS/IVUS) device, which can employ very small transducers arranged on a catheter and provides electronic transduced echo signals to an external imaging system in order to produce a two or three-dimensional image of the lumen, the arterial tissue, plaque, blockages, and/or tissue surrounding the artery. These images can be generated in substantially real time and can provide images of superior quality to the known x-ray imaging methods and apparatuses. Other imaging methods and intravascular ultrasound imaging applications would also benefit from enhanced image resolution. An ultrasound device, for example, can include a flexible polyimide film layer.

Imaging device 260 can be coupled with a number of wires and/or fiber optics that extend through catheter body 205 toward the proximal end of catheter 200. For example, for IVUS imaging devices, seven braided wires can be used. Some or all of these wires, for example, can have a diameter less than 0.01 inches.

Figure 3A:
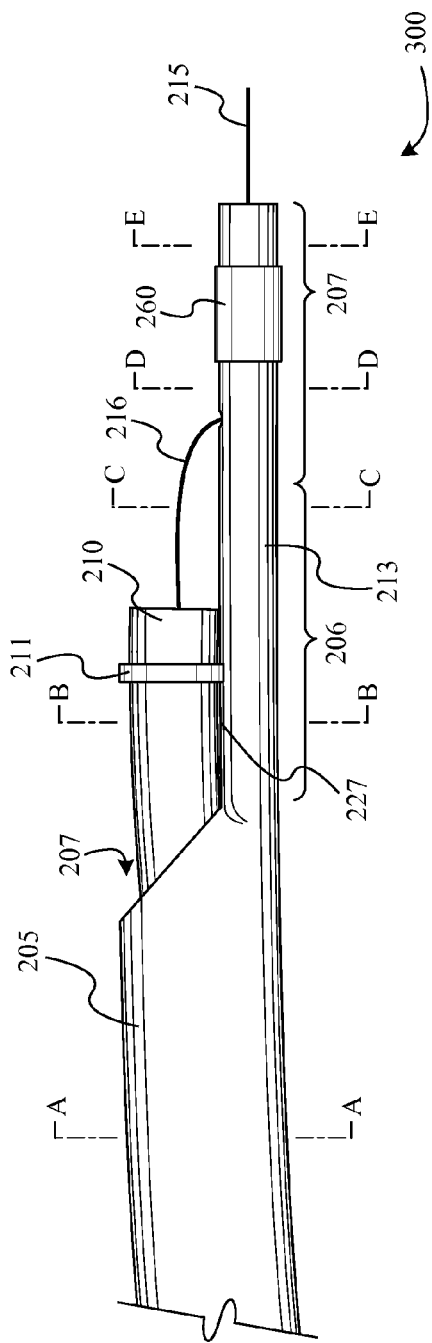
FIG. 3A shows a side view of a laser catheter according to one embodiment of the invention.

FIG. 3A shows laser catheter 300 according to another embodiment of the invention. Laser catheter 300 can include a catheter body 205 (or sheath) within which a fiber optic bundle 210 (or any other light guide) is disposed. Fiber optic bundle can include any number of optical fibers and, in some embodiments, can include a separate sheath. Catheter body 205 can include a distal end and a proximal end. The proximal end of catheter body 205 can include a coupler that is configured to couple with a laser source as shown in FIG. 1. The proximal end of the fiber optic bundle can also be coupled with the coupler in order to receive and conduct laser light through the optical fibers. The distal end of catheter body 205 includes opening 207 from which the distal end of fiber optic bundle 210 extends. Fiber optic bundle can include a marker band 211 at the distal tip of the fiber optic bundle that can include any number of sizes and/or shapes. Marker band 211, for example, can include a radiopaque material.

Catheter body 205 can include tip 213, that extends from opening 207. In some embodiments, tip 213 can be coupled with catheter body 205. In other embodiments, tip 213 can be integral with catheter body 205. In some embodiments, tip 213 can support the distal end of fiber optic bundle 210. Fiber optic bundle 205 can include a guidewire lumen that extends through a portion of the catheter body. During use guidewire 215 can be positioned within a vessel, laser catheter 200 can be threaded over guidewire 215 using the guidewire lumen in order to direct the catheter through a vessel toward a target. In some embodiments, guidewire lumen can extend through at least a portion of tip 213. Retaining wire 216 can extend from the distal tip of fiber optic bundle 210 and be coupled with tip 213. In some embodiments, retaining wire 216 and guidewire can be the same wire.

In some embodiments, tip 213 can also include an imaging device 260 disposed at the distal end of tip 213. Imaging device 260 can be located at least 0.4, 0.5, 0.6, 0.7, 0.8, 0.9, 1.0 cm longitudinally (or forward) from the distal end (or exit aperture) of fiber optic bundle 210. Any type of imaging device can be used.

Imaging device 260 can include any ultrasound sensor or laser interferometry device. A laser interferometry device can include a plurality of fiber optics with an exit aperture disposed near the distal end of the laser catheter and extending through a sheath of the catheter. Imaging device 260, for example, can be formed cylindrically around tip 213 as a patch, or a ring. In some embodiments, imaging device 260 can include any shape or size.

Figure 3B:
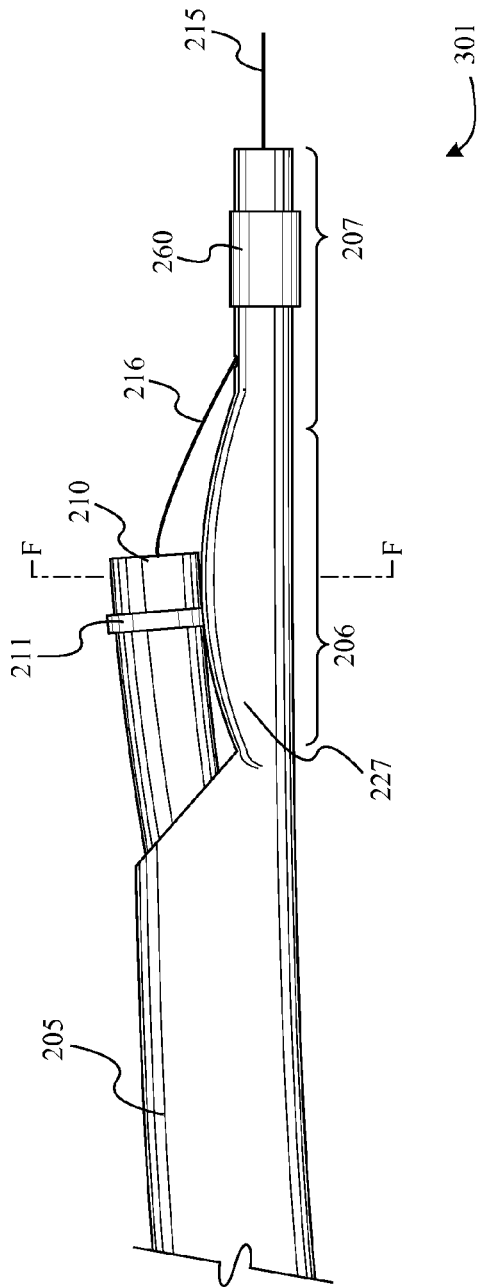
FIG. 3B shows a side view of a balloon laser catheter according to one embodiment of the invention.

In some embodiments, balloon 227 can be disposed between fiber optic bundle 210 and tip 213. In FIG. 3A balloon 227 is in the deflated state and not shown. Balloon 227 can be coupled with a balloon tube that can be used to inflate and/or deflate the balloon. Balloon tube can extend proximally through at least a portion of catheter body 205. In some embodiments, a balloon tube coupler can be provided that allows a doctor to attach a syringe (or other device) that can be activated to inflate and/or deflate the balloon. FIG. 3B shows an example of laser catheter 300 with balloon 227 inflated. As seen, balloon 227 can be inflated in order to laterally shift the exit aperture of fiber optic bundle 210 relative to tip 213.

Figure 4A:
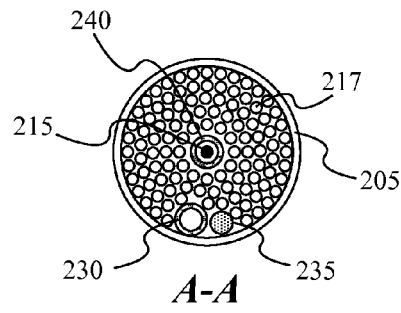
FIG. 4A shows a cross section of the catheter in FIG. 3A along line A-A.

FIG. 4A shows a cross section of catheter 300 along line A-A according to some embodiments. As shown, catheter body 205 surrounds a plurality of fiber optics 217, guidewire lumen 240, balloon tube 230, and imaging wire bundle 235. In some embodiments, balloon tube 230 can have an outside diameter of about 0.008, 0.009, 0.010. 0.011, 0.012, 0.013, 0.014, or 0.015 inches. Any of these components may be included in a different combination or order, or excluded altogether. Guidewire 215 is shown within guidewire lumen 240. In some embodiments, balloon tube 235 and/or guidewire lumen 230 can be disposed within a sheath and/or a tube.

Figure 4B:
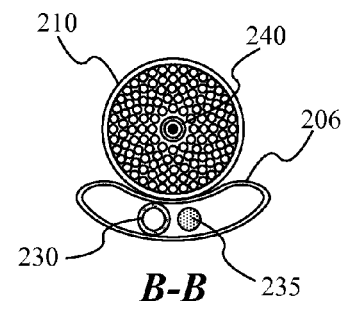
FIG. 4B shows a cross section of the catheter in FIG. 3A along line B-B.

FIG. 4B shows a cross section of catheter 200 along line B-B according to some embodiments. In this embodiment, tip 213 includes balloon 206 in a deflated state. At some point, balloon tube 230 terminates within or at the boundary of balloon 206. Thus, balloon tube 230 can terminate at a number of different positions within balloon 206. Imaging wire bundle 235 extends through balloon 206. The junctions of imaging wire bundle 235 and balloon 206 can be sealed to ensure balloon inflates without a leak at the junction. Guidewire lumen 240 is placed concentrically within catheter body 205. In other embodiments guidewire lumen 240 can be located anywhere within catheter body 205, for example, guidewire lumen can be disposed eccentrically with catheter body (e.g., as shown in FIG. 6B). In some embodiments, guidewire lumen 230 can extend through balloon when a retaining wire is used.

Figure 4C:
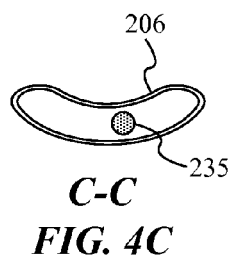
FIG. 4C shows a cross section of the catheter in FIG. 3A along line C-C.
Figure 4D:
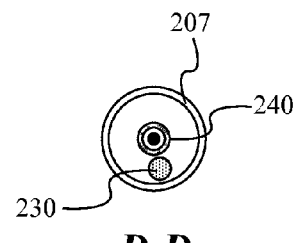
FIG. 4D shows a cross section of the catheter in FIG. 3A along line D-D.

FIG. 4C shows a cross section of catheter 200 along line C-C according to some embodiments. At this point, balloon tube 230 terminated within balloon 206 and only wire bundle 235 is found within balloon 206. FIG. 4D is a cross section of catheter 200 along line D-D showing imaging wire bundle 230 extending through tip 213 distal from balloon 206 according to some embodiments. In some embodiments, guidewire lumen 230 can extend through balloon when a retaining wire is used.

Figure 4E:
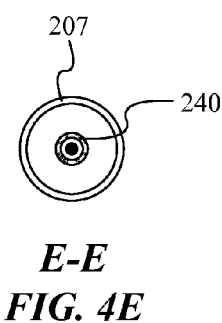
FIG. 4E shows a cross section of the catheter in FIG. 3A along line E-E.
Figure 4F:
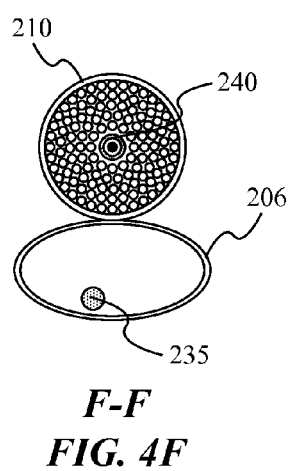
FIG. 4F shows a cross section of the catheter in FIG. 3B along line F-F.

FIG. 4E is a cross section of catheter 200 along line E-E. Line E-E is distal relative to probe 260. Hence, distal tip portion 207 only includes guidewire lumen 240. In some embodiments, distal tip portion 207 can have an inside diameter similar or slightly larger than the outside diameter of guidewire lumen 240. FIG. 4F shows a cross section of catheter 210 in FIG. 3B along line F-F. Imaging wire bundle 235 is shown passing through balloon 206 while inflated.

In some embodiments, catheter body 205 may have a diameter of approximately 2.0 mm. Each fibers 217, for example, may be less than about 0.1 mm. As another example, the fibers may be less than about 0.05 mm. The fiber optics may be contained within bundle 210. For example, bundle 210 can be about 1.0 mm by about 2.0 mm. Guidewire lumen 230, for example, can have an inside diameter of approximately 0.024 inches and inside diameter of approximately 0.018 inches. In other embodiments, guidewire lumen 230 may have an outside diameter less than about 0.025 inches and/or an inside diameter less than about 0.02 inches.

While a fiber optic bundle 210 is shown in the figures, any type of light guide can be used. For example, a liquid light guide and or a solid light guide can be used in place of the fiber optic bundle without limitation.

Figure 5A:
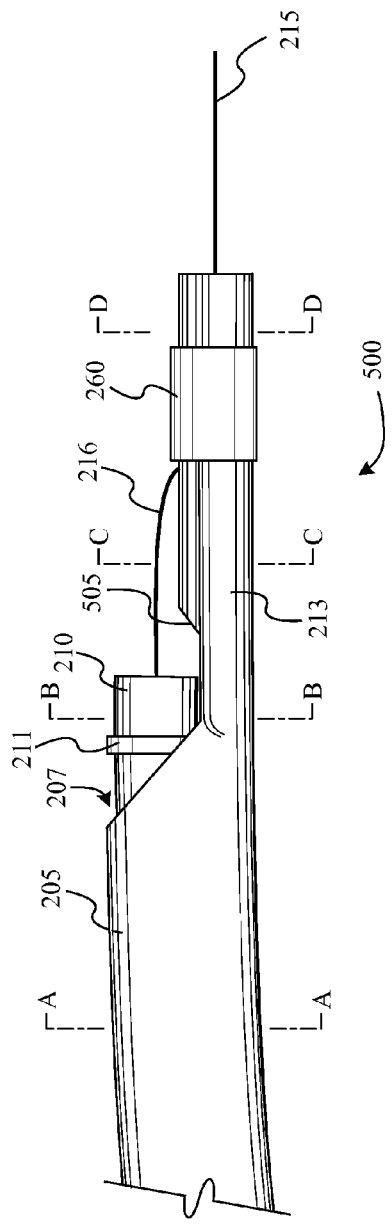
FIG. 5A shows a side view of a laser catheter with a ramp according to one embodiment of the invention.
Figure 5B:
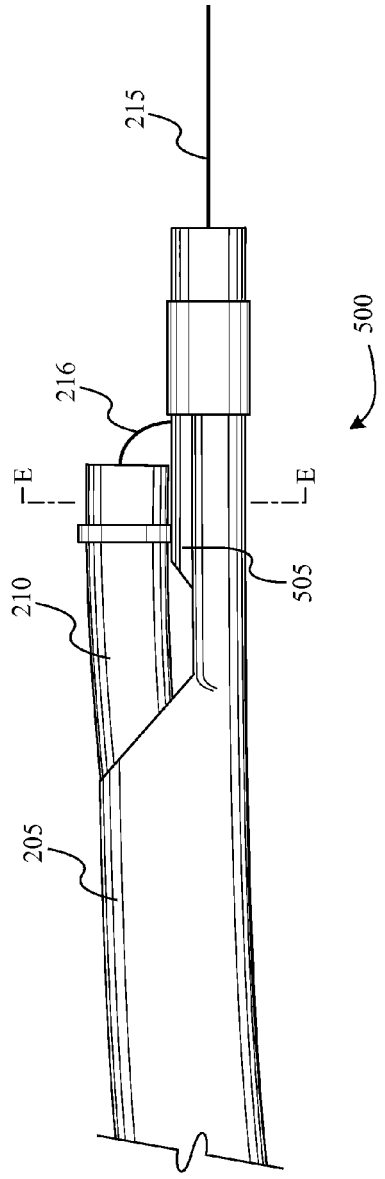
FIG. 5B shows a side view of an engaged laser catheter with a ramp according to one embodiment of the invention.

FIG. 5A shows a side view of laser catheter 500 with ramp 505 according to one embodiment of the invention. Imaging device 260 can be found at the distal tip of the catheter body 205 forward (more distal) than the distal tip of fiber optic bundle 210. Fiber optic bundle 210 can be located at a first position relative to ramp 505 and can extend from aperture 207 of catheter body 205. Fiber optic bundle can be actuated forward into a second position as shown in FIG. 5B, such that distal end of fiber optic bundle 210 has actuated distally up and past ramp 505 toward the distal end of catheter 500. Retaining wire 216 can provide a restraining force on the distal end of fiber optic bundle 210 in order to keep the distal end substantially parallel with catheter body 205 while in the second position. In some embodiments, guidewire 215 can extend through a guidewire lumen through catheter body 205. In other embodiments, retaining wire 216 and guidewire 215 can be the same wire.

In some embodiments that include retaining wire 216, retaining wire 216 may be detachably coupled with either or both distal tip 213 and/or light guide 210. For example, retaining wire 216 may be connected with the distal tip using solder, clamps, glue, fused, etc. In some embodiments, retaining wire is soldered with radiopaque marker band 211. In other embodiments, retaining wire 216 may be coiled around the distal tip and glued or fused with distal tip 213. In some embodiments, retaining wire 216 may be sandwiched between distal tip 213 and radiopaque marker band 211. In some embodiments, retaining wire 216 may extend through a portion of light guide 210. For example, retaining wire 216 may extend through light guide 210 next to and/or with a plurality of optical fibers. Retaining wire 216 may aid in retaining the position and/or bias of the light guide when light guide is extended up ramp 505. Retaining wire 216 may also aid in providing the proper bias when light guide is extended up ramp 505. For example, retaining wire 216 may be lengthened and/or include elasticity such that biasing catheter may be more or less biased when light guide is extended up ramp 505. In some embodiments, retaining wire provides resistance to light guide 210 when balloon 705 is inflated and/or when light guide is extended up ramp 505, which may align light guide 210 parallel with distal tip 213 and/or catheter body 205.

Various other configurations of biasing laser catheters can be used. In some embodiments, laser catheters described in U.S. Pat. No. 7,572,254, entitled "Rapid Exchange Bias Laser Catheter Design," which is incorporated herein by reference in its entirety, can be used in conjunction with various aspects described herein. Similarly, the laser catheters described in U.S. patent application Ser. Nos. 12/406,807, entitled "Apparatus and Methods for Directional Delivery of Laser Energy;" Ser. No. 12/265,441, entitled "Biasing Laser Catheter: Monorail Design;" Ser. No. 12/337,190, entitled "Eccentric Balloon Laser Catheter;" and/or Ser. No. 12/337,232, entitled "Rapid Exchange Bias Laser Catheter Design," each of which are incorporated herein by reference in their entirety, can also be used in conjunction with various aspects described herein. For example, laser catheters described in any of the documents incorporated by reference can be implemented with a distal imaging device.

Figure 6A:
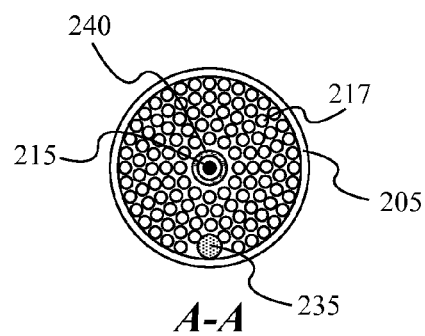
FIG. 6A shows a cross section of the catheter in FIG. 5A along line A-A.
Figure 6B:
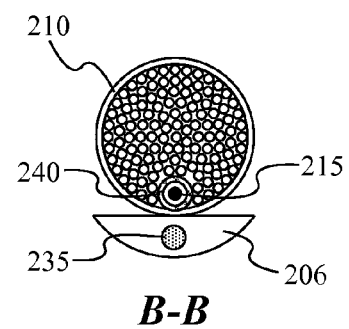
FIG. 6B shows a cross section of the catheter in FIG. 5A along line B-B.

FIG. 6A shows a cross section of catheter 500 along line A-A. Catheter body 205 surrounds a number of fiber optics 217, guidewire lumen 240, and imaging wire bundle 235. Any of these components may be included in a different combination, order, or excluded altogether. In some embodiments, guidewire lumen 240 can be positioned at any position within the catheter body. In some embodiments, balloon tube 235 and/or guidewire lumen 230 can be disposed within a sheath and/or a tube. In some embodiments, fiber optics 217 and/or guidewire lumen 240 can be bundled within a sheath. Thus, when the fiber optic bundle is actuated forward fiber optics 217 do not tangle with balloon lumen 235. Moreover, balloon lumen, in some embodiments, can be embedded within catheter body 205.

Figure 2B:
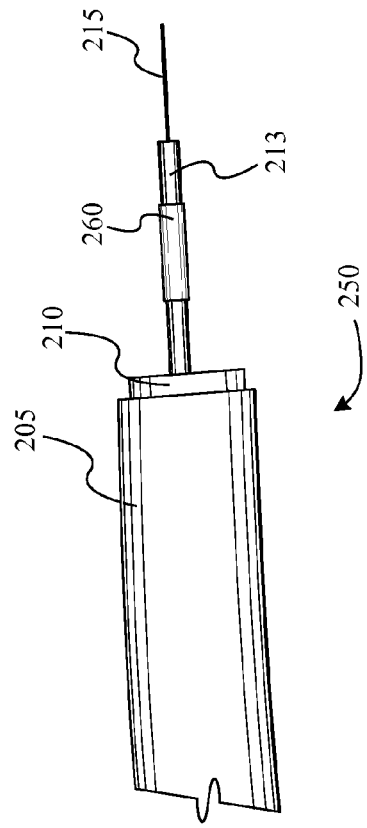

FIG. 6B shows a cross section of catheter 500 along line B-B. In some embodiments, guidewire lumen 217 is arranged eccentrically within fiber optic bundle 210 as shown in the figure. Guidewire 215 is shown within guidewire lumen 240. In other embodiments guidewire lumen 240 can be located anywhere within catheter body 205, for example, guidewire lumen can be disposed concentrically within catheter body (e.g., as shown in FIG. 2B). Imaging wire bundle 235 also extends through this portion of catheter 500.

Figure 6C:
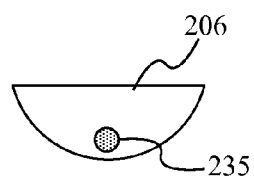
FIG. 6C shows a cross section of the catheter in FIG. 5A along line C-C.
Figure 6D:
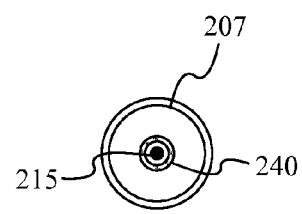
FIG. 6D shows a cross section of the catheter in FIG. 5A along line D-D.
Figure 6E:
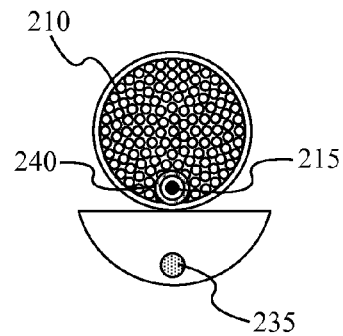
FIG. 6E shows a cross section of the catheter in FIG. 5B along line E-E.

FIG. 6C shows a cross section of catheter 500 along line C-C. This portion of catheter 500 includes tip 213 that extend more distally from aperture 207 and proximal to imaging device 260. Imaging wire bundle 235 also extends through this portion of catheter 500. FIG. 6D shows a cross section of catheter 500 along line D-D. This portion of catheter 500 is distal with respect to imaging device 260 and only the guidewire lumen 240 extends through this portion. FIG. 6E shows a cross section of catheter 500 along line E-E showing fiber optic bundle 210 having been actuated up the ramp as shown in FIG. 5B.

FIG. 7A shows a side view of balloon catheter 700 with balloon 705 deflated according to another embodiment of the invention. In the deflated state, balloon catheter 700 is somewhat similar to catheter 200 shown in FIG. 3A. However, balloon catheter 700 differs from catheter 200 in that balloon 705 inflates radially as shown in FIG. 7B. In some embodiments, a physician can oblate blockage within a vessel (e.g., a human artery) using catheter 700. Catheter 700 can be positioned in front of the blockage with balloon 705 deflated. The laser can then be activated. During lasing catheter 700 can ablate a central portion of the blockage roughly the size of the exit aperture of catheter 210. In order to ablate portions of the blockage near the vessel's interior walls, balloon 705 can be inflated and pressed against an interior wall within the vessel. The pressure against the interior wall can shift the exit aperture of catheter 210 toward the opposite interior wall within the vessel allowing catheter 700 to ablate material near the vessel wall by activating the laser. Catheter 700 can be rotated by the physician in order to ablate the material near other portions of the interior wall of the vessel.

In some embodiments, catheter 700 can include imaging device 260 and in other embodiments imaging device 206 can be excluded. Similarly, catheters in some embodiments can include radiopaque band 211, while catheters in other embodiments do not.

Figure 8:
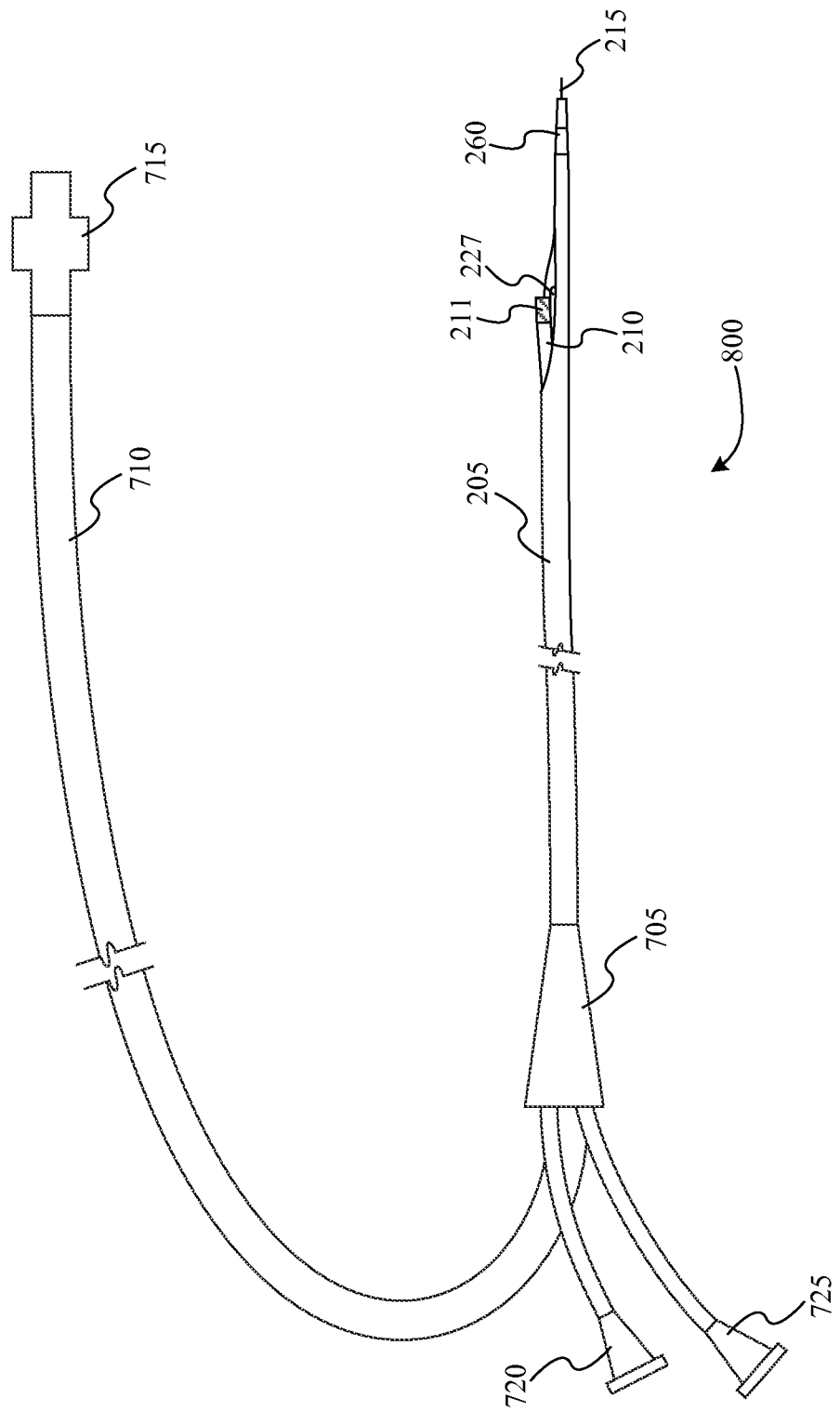
FIG. 8 is a side view of a balloon biasing catheter according to one embodiment.

FIG. 8 is a side view of balloon biasing catheter 800 according to one embodiment. A balloon biasing catheter may include a catheter body 205 (or elongated housing) with a light guide 210 disposed within a lumen of catheter body 205 and extending from an aperture within catheter body 205. For example, light guide 210 may include a plurality of fiber optics. As another example, the light guide may be a liquid light guide and/or a combination of a liquid light guide and a fiber optic light guide. In some embodiments, the light guide is free to slide within the lumen of the catheter body. In some embodiments, the light guide lumen may slide relative to the catheter body. In other embodiments, the light guide may be fixed within the lumen of the catheter body. Light guide 210 may be located within catheter body 205 and may extend from the proximal end of the catheter body to the distal end of the catheter body. At the proximal end of the catheter body, light guide 210 may terminate with laser coupler 715. The light guide lumen may include an aperture at or near the distal end of catheter body 205 from which light guide 210 may extend. In some embodiments, light guide 210 may extend 1-10 mm from the aperture. In some embodiments, light guide 210 may also include a radiopaque marker band 211 near the distal end.

A balloon biasing catheter may also include a guidewire lumen. The guidewire lumen may be configured to allow a guidewire to pass and/or slide therethrough. In some embodiments, the guidewire lumen may extend, for example, from distal guidewire port through a portion of catheter body 205. In some embodiments, the guidewire lumen may extend to or near the proximal end of catheter body 205. In other embodiments, guidewire lumen may extend from the distal end to a position proximal with the light guide aperture and/or proximal with balloon 227. The guidewire lumen may be configured to accept a guidewire and allow the guidewire to slide within the guidewire lumen. Proximal guidewire port 720 may be located anywhere along catheter body 205.

In some embodiments, catheter 800 can include balloon tube port 725 that can be coupled with balloon 227 via a balloon tube (e.g. balloon tube 230). In some embodiments balloon lumen may couple with a luer fitting at balloon tube port 725. Balloon tube port 725 can be configured to accept any type of syringe or pump that can pressurize and depressurize balloon 227. For example, the inner diameter of balloon lumen may be approximately 0.001 inches. In some embodiments, the inner diameter of the balloon lumen (or tube) may be between 0.0005 and 0.01 inches. The outside diameter of the balloon lumen, for example, may be 0.016 inches. In some embodiments, the outside diameter of the balloon lumen may be 0.05 to 0.005 inches. At balloon port or luer, the balloon may be coupled with a syringe or an indeflator. Balloon 705 may be inflated by injecting fluid through balloon lumen using either a syringe or an indeflator. In some embodiments, the balloon may be inflated using a contrast agent fluid or saline solution. The balloon lumen 1813 may include any type of plastic tubing known in the art. For example, balloon lumen 1813 may comprise nylon, Teflon, polyethylene, etc.

Guidewire lumen port 720 can also be included. Guidewire lumen port 720 can be coupled with guidewire lumen 240 and can allow a guidewire to extend through the distal end toward the proximal end of the catheter. A bifurcated cover can be used to separate the ports from the body of the catheter.

FIG. 9A shows a cutaway of a balloon biasing catheter in use within vessel 810 near target 805. The balloon biasing catheter may be inserted into vessel 810 by following guidewire 215 that may have been previously placed within vessel 810. Guidewire 215 may run through the guidewire lumen as shown in the figure. Balloon 705 is deflated in FIG. 9A. Light guide 210 may be activated and a portion of target 215 may be ablated. FIG. 18B shows results of ablation of target 805 with the balloon biasing catheter positioned as shown in FIG. 9A. Target 805 may not be completely ablated leaving portions 806, 807. In some embodiments, a hole within target 805 may result.

FIG. 9B shows light guide 210 biased axially by inflating balloon 705. When balloon 705 is inflated, the laser catheter can be axially biased toward target portion 807. Moreover, balloon 705 may be partially or fully inflated as needed to align light guide 210 with target portion 807. FIG. 10A shows a resulting example of ablation using the configuration in FIG. 9B. Target portion 807 has been at least partially ablated. In some embodiments, target portion 807 may be completely ablated.

After ablation of target portion 807, balloon 705 can be deflated and the catheter rotated within vessel 810 as shown in FIG. 10A. As shown in FIG. 10B, balloon 705 can be inflated positioning light guide 210 toward target portion 806. In some embodiments, balloon 705 may remain inflated during rotation. In some embodiments, balloon biasing catheter and/or guidewire 215 may be advanced during any of the ablation steps. In some embodiments, balloon biasing catheter may be rotated 90° or any other angle in order to ablate other target portions and/or material near or adhering to a vessel wall. In some embodiments, during ablation as shown in FIGS. 9A, 9B, 10A and 10B, imaging of the interior of vessel 810 can occur using imaging device 260.

In some embodiments, laser catheters can include a balloon (e.g., balloon 705). Such balloons, for example, can have a diameter of about 1 mm to 3 mm when inflated. In some embodiments, balloon may have an inflated diameter up to about 5 mm and as little as 0.5 mm. In some embodiments, the balloon may comprise a portion of tubing with a sealed distal end. In some embodiments, a portion of tubing may form the balloon and have thinner walls and/or a larger diameter such that the balloon portion of the tubing inflates under pressure. A balloon, for example, may comprise any type of plastic, for example, the balloon may comprise nylon, Teflon, polyethylene, etc. A balloon, in some embodiments, may extend the entire length of distal tip 213. For example, balloon 705 may be 10 cm, 9 cm, 8 cm, 7 cm, 6 cm, 5 cm, 4 cm, 3 cm, 2 cm, or 1 cm in length.

In some embodiments, a balloon can be used to deflect a light guide, fiber optic bundle and/or catheter body. In doing so, the balloon, for example, may deflect the light guide, fiber optic bundle and/or catheter body 205 1.0 mm. In other embodiments, the light guide, fiber optic bundle and/or catheter body may be biased 0.5 mm, 1.5 mm, 2.0 mm, 2.5 mm, 3.0 mm etc. from a deflated position. By biasing the light guide, fiber optic bundle and/or catheter body, the balloon biasing catheter may ablate a larger diameter area than if the light guide is not biased.

Figure 11:
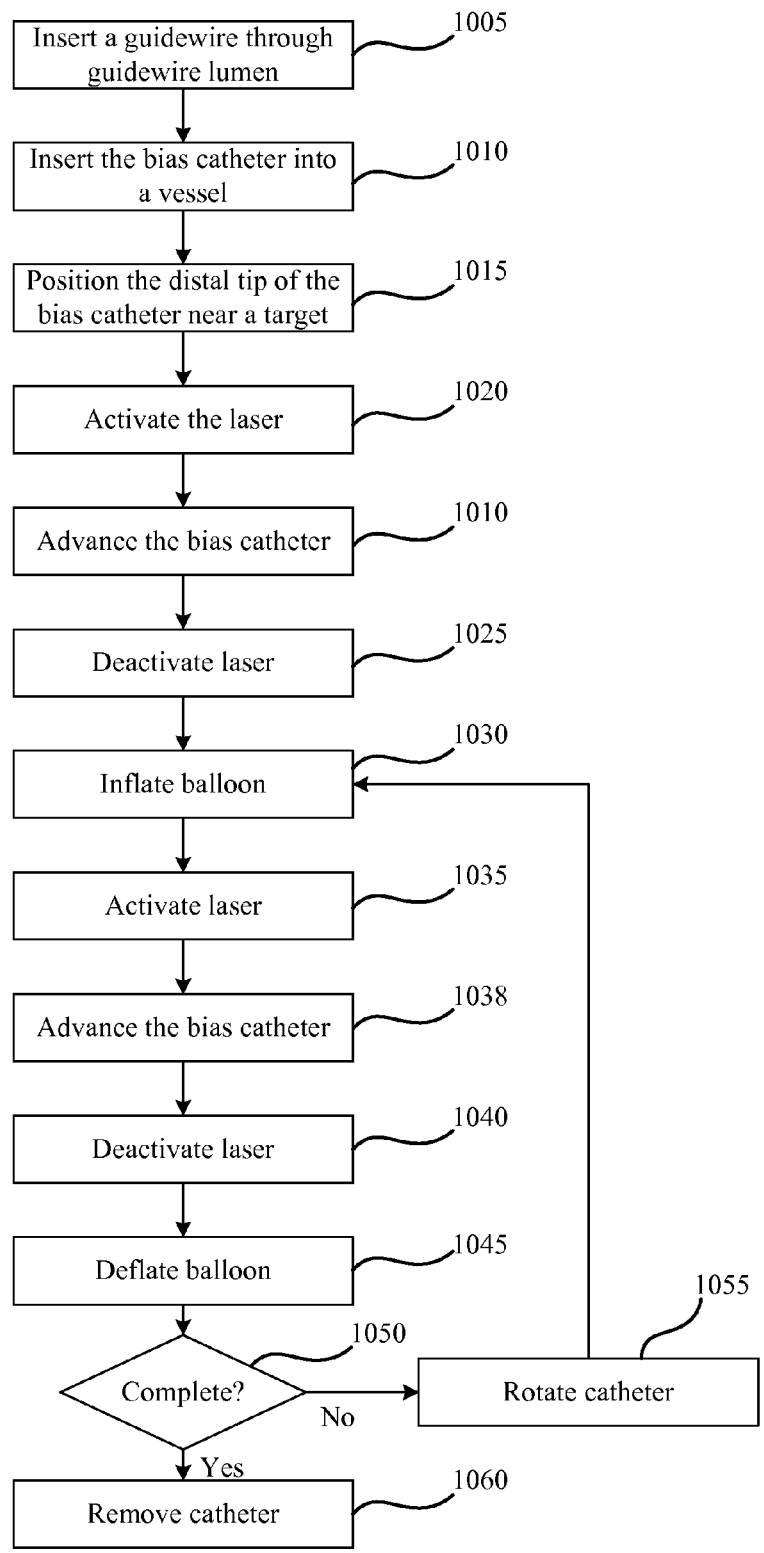
FIG. 11 is a flowchart describing one embodiment for using a biasing catheter.

FIG. 11 shows a flowchart of a process for using a biasing catheter according to one embodiment. Various other processes may be used that add to or take away from the process shown in FIG. 11 and described below. The proximal end of a guidewire is inserted through the distal guidewire port at the distal tip of the balloon biasing catheter at block 1005. The balloon biasing catheter may then be inserted into a vessel at block 1010 and slid over the guidewire and positioned near a target at block 1015. At block 1020 the laser may be activated ablating a portion of the target area. The balloon biasing catheter may be advanced at block 1023. Once ablation is complete, the laser is deactivated at block 1025. If portions of the target are not completely ablated, for example, if material remains near the vessel walls, then the balloon may be inflated at block 1030. When the balloon is inflated the distal tip of the balloon biasing catheter may be radially biased yet substantially parallel with the balloon biasing catheter and positioned to ablate unablated portions of the target. The laser may again be activated at block 1035 and portions of the target ablated. At block 1038 the balloon biasing catheter may be advanced toward the target. At block 1040 the laser is deactivated after a period of time and the balloon deflated at block 1045. If the ablation area is satisfactory and no more ablation is required as decided at block 1050 the balloon biasing catheter is removed at block 1060. However, if more ablation is required, the balloon biasing catheter may be rotated axially within the vessel at block 1055 and the process returns to block 1030.

Figure 12:
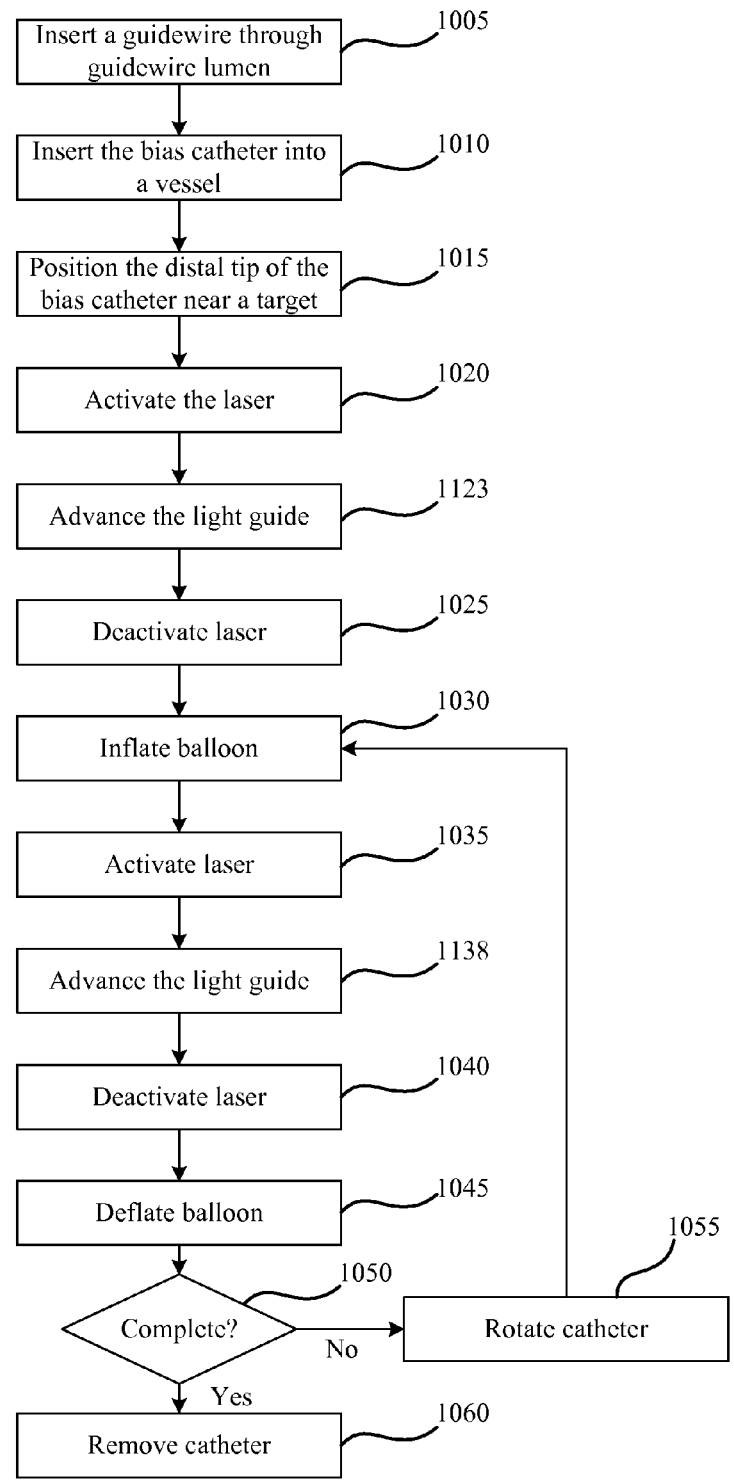
FIG. 12 is another flowchart describing another embodiment for using a biasing catheter.

FIG. 12 shows a flowchart of a process for using a biasing catheter according to one embodiment. This flow chart is substantially similar to the flowchart shown in FIG. 11. In this embodiment, however, at blocks 1123 and 1138 the light guide is advanced relative to the balloon biasing catheter. In such embodiments, the catheter body remains substantially still as the light guide is advanced to ablate target material.

While FIG. 11 and FIG. 12 are described in conjunction with a balloon biasing catheter, other types of biasing catheters can be used. For example, biasing catheters as those shown in FIG. 5A can also be used.

Figure 13:
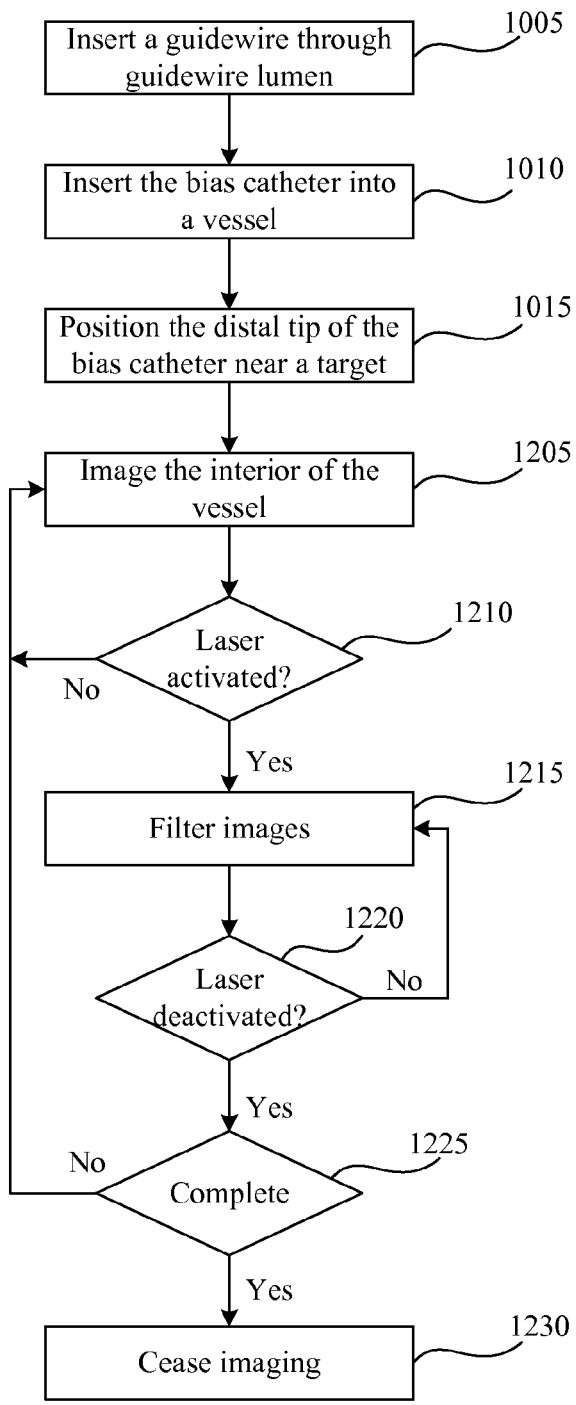
FIG. 13 is a flowchart describing another embodiment for using a biasing catheter in conjunction with an imaging device.

FIG. 13 is a flowchart describing another embodiment for using a biasing catheter in conjunction with an imaging device. Blocks 1005, 1010, and 1015 are similar to those described above in conjunction with FIG. 11. According to some embodiments, once the bias catheter has been positioned within a vessel (e.g., at block 1015), the interior of the vessel can be imaged using an imaging device (e.g., an ICUS/IVUS device). In some embodiments, the image of the interior of the vessel can be displayed on a display (e.g., the display associated with computer 180 shown in FIG. 1) such that a physician or doctor can view the interior of the vessel. In some embodiments, based on the image provided, the doctor can reposition the laser catheter.

At block 1210 if the laser is activated images produced by the imaging device can be filtered at block 1215. In some embodiments, the filtering can occur in real time. In other embodiments, the filtering can occur after the imaging has occurred. In some embodiments, filtering can occur by disabling the imaging device while the laser is activated. Moreover, imaging can be filtered for an extended period of time beyond the time the laser is activated. Filtering can also occur at a display, such that, images produced while the laser is activated are not displayed to a user. If the laser is not activated at block 1215, the interior of the vessel can continued to be imaged at block 1210.

At block 1220, if the laser is not deactivated, images of the interior of the vessel can continue to be filtered at block 1215. Otherwise, the process continues to block 1225. At block 1225, if the procedure is not complete, the process returns to block 1205, otherwise imaging ceases at block 1230.

Various embodiments disclosed herein describe the use of an imaging device in conjunction with a laser catheter. Any type of imaging can be used. For example, the imaging device can include an ultrasound sensor or a laser interferometry device. A laser interferometry device can include a plurality of fiber optics with an exit aperture disposed near the distal end of the laser catheter and extending through a sheath of the catheter. The imaging device, for example, can be formed cylindrically, as a patch, or a ring.

An ultrasound device can include an Intracoronary/Intravascular Ultrasound (ICUS/IVUS) device that can employ very small transducers arranged on a catheter and provides electronic transduced echo signals to an external imaging system in order to produce a two or three-dimensional image of the lumen, the arterial tissue, plaque, blockages, and/or tissue surrounding the artery. These images can be generated in substantially real time and can provide images of superior quality to the known x-ray imaging methods and apparatuses. Other imaging methods and intravascular ultrasound imaging applications would also benefit from enhanced image resolution. An ultrasound device, for example, can include a flexible polyimide film layer.

In some embodiments of the invention, imaging can be gated while the laser catheter is pulsing. Signal processing techniques can be implemented (e.g. at computer 180 in FIG. 1) that filters out optical, mechanical, and electronic interference effects. An electron plasma can be created within the vessel during ablation. This electron plasma can interfere with imaging from an imaging device (e.g. imaging device 260). In some embodiments, electromagnetic interference can be avoided by filtering out data during the set time period while the laser is pulsing. In other embodiments, filtering can occur for a longer duration such as for a period greater than the pulsing period. For example, filtering can occur 30%, 40%, 50%, 60%, or 70% longer than the laser pulsing period in order to filter out any latent electromagnetic interference. For example, if the laser pulses laser light for 135 ns, filtering can eliminate imaging data during the 200 ns after the beginning of the pulse and/or data capture can be delayed for 200 ns after the beginning of the pulse.

Moreover, photochemical effects in an area ablated by a laser catheter can remain for up to about 0.6 ms. Thus, imaging data recorded using a forward imaging device can also include filtering data recorded 0.4, 0.5, 0.6, 0.7, 0.8, 1.0, 1.1, 1.2, 1.3 or 1.4 ms after the laser pulse has begun. Thus, for example, signal capture (or data retention) can begin after 1.0 ms after the beginning of the laser pulse. Delaying signal capture until 1 ms after the laser pulse still allows for a better than 10 frames per second data acquisition and signal processing even operating at 80 Hz.

In some embodiments, elimination of data using filtering techniques can be implemented in software operating at computer 180. In other embodiments, dedicated electrical circuitry can be used to filter the data after the data has been received. In some embodiments, data filtering can occur well after the imaging data has been captured and recorded. In yet other embodiments, filtering can occur in real time. That is, for example, the data from the imaging device can be ignored, deleted, or not displayed while the laser is active and/or during some post activation time period. As another example, the imaging device can be disabled during filtering periods. In other embodiments, gating can prevent images from being displayed on a display (e.g., a display associated with computer 180 shown in FIG. 1) while the laser catheter is activated.

In some embodiments, the laser can be electrically, mechanically, or optically interrupted to allow for data acquisition. For example, imaging can occur at predetermined intervals during which laser pulses are stopped to allow for better imaging. As another example, imaging can be initiated by a doctor or technician. During this time, the laser can be deactivated to allow for better imaging. Once imaging is complete, the laser can be reactivated and pulsing can recommence (whether automatically or manually).

Circuits, logic modules, processors, and/or other components may be described herein as being "configured" to perform various operations. Those skilled in the art will recognize that, depending on implementation, such configuration can be accomplished through design, setup, interconnection, and/or programming of the particular components and that, again depending on implementation, a configured component might or might not be reconfigurable for a different operation. For example, a programmable processor can be configured by providing suitable executable code; a dedicated logic circuit can be configured by suitably connecting logic gates and other circuit elements; and so on.

While embodiments of the invention are described herein with reference to particular blocks, it is to be understood that the blocks are defined for convenience of description and are not intended to imply a particular physical arrangement of component parts. Further, the blocks need not correspond to physically distinct components.

While the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present invention may be encoded on various computer readable storage media; suitable media include magnetic disk or tape, optical storage media such as compact disk (CD) or digital versatile disk (DVD), flash memory, and the like. Computer readable storage media encoded with the program code may be packaged with a compatible device or provided separately from other devices. In addition program code may be encoded and transmitted via wired optical, and/or wireless networks conforming to a variety of protocols, including the Internet, thereby allowing distribution, e.g., via Internet download.

What is claimed is:

1. A laser catheter comprising:
 a catheter body having a central axis, a proximal end and a distal end, the catheter body having a lumen disposed between the proximal end and the distal end, the lumen having a distal opening at the distal end;

a light guide having a proximal end and a distal end, the light guide being at least partially disposed within the lumen and the distal end of the light guide extending from within the distal opening of the catheter body, wherein the light guide is configured to conduct light from a laser source at the proximal end to the distal end of the light guide;

a tip extending distally from the distal end of the catheter body, wherein the tip is disposed eccentrically to the light guide; and an ultrasound imaging device disposed on the tip and positioned distally from the distal opening of the catheter body and the distal end of the light guide.

2. The laser catheter according to claim 1, further comprising a plurality of wires coupled with the ultrasound imaging device, wherein the wires extend through the tip and the catheter body and emerge from the proximal end of the catheter body.

3. The laser catheter according to claim 1, wherein the ultrasound imaging device comprises a probe.

4. The laser catheter according to claim 2, further comprising a wire tube disposed within the catheter body within which the plurality of wires are disposed.

5. The laser catheter according to claim 1, wherein the ultrasound imaging device is configured to image when the light guide is not conducting light.

6. The laser catheter according to claim 1, wherein the ultrasound imaging device is disposed at least 0.9 cm from the distal end of the light guide.

7. The laser catheter according to claim 1, further comprising a ramp disposed on the tip, wherein the light guide is longitudinally moveable relative to the catheter body, and wherein the lateral position of the distal end of the light guide relative to the central axis of the catheter body is moveable by sliding the light guide longitudinally over the ramp.

8. The laser catheter according to claim 1, further comprising a balloon positioned near the distal opening and disposed proximate with the distal end of the light guide, wherein the lateral position of the distal end of the light guide relative to the central axis of the catheter body is moveable by inflating the balloon.

9. The laser catheter according to claim 1, further comprising a balloon disposed on the catheter body.

10. The laser catheter according to claim 8, further comprising a balloon inflation tube coupled with the balloon, wherein the balloon inflation tube extends through the catheter body.

11. The laser catheter according to claim 1, wherein the light guide comprises a plurality of optical fibers arranged concentrically about the central axis of the catheter body.

12. The laser catheter according to claim 1, wherein the light guide comprises a plurality of optical fibers arranged eccentrically about the central axis of the catheter body.

13. The laser catheter according to claim 1, further comprising a guide wire lumen extending through the catheter body.

14. The laser catheter according to claim 1, further comprising a guide wire lumen extending through at least a portion of the tip.

* * * * *